(12) United States Patent
Clark

(10) Patent No.: US 6,778,307 B2
(45) Date of Patent: Aug. 17, 2004

(54) METHOD AND SYSTEM FOR PERFORMING SWEPT-WAVELENGTH MEASUREMENTS WITHIN AN OPTICAL SYSTEM

(75) Inventor: Bryan Clark, Mountain View, CA (US)

(73) Assignee: Beyond 3, Inc., Mountain View, CA (US)

(*) Notice: Subject to any disclaimer, the term of this patent is extended or adjusted under 35 U.S.C. 154(b) by 0 days.

(21) Appl. No.: 10/403,238

(22) Filed: Mar. 28, 2003

(65) Prior Publication Data

US 2003/0184867 A1 Oct. 2, 2003

Related U.S. Application Data

(63) Continuation-in-part of application No. 09/789,913, filed on Feb. 21, 2001, now Pat. No. 6,522,471.

(51) Int. Cl.[7] .............................. G02F 1/00; G02F 1/03; G01B 9/02; H01S 3/10; G01N 21/86
(52) U.S. Cl. ..................... 359/237; 359/245; 359/260; 356/237.2; 356/450; 356/519; 356/5.05; 372/20; 250/559.11; 250/559.27
(58) Field of Search ................................ 359/237, 245, 359/260, 629, 318; 356/237.2, 237.1, 237.3, 450, 479, 519, 502, 5.05, 5.15; 372/20, 32; 250/559.11, 559.27, 559.28, 559.42

(56) References Cited

U.S. PATENT DOCUMENTS

| | | | |
|---|---|---|---|
| 3,521,956 A | * 7/1970 | Froome et al. | 356/5.15 |
| 3,885,874 A | * 5/1975 | Haas et al. | 356/450 |
| 3,901,597 A | 8/1975 | White | |
| 4,659,224 A | 4/1987 | Monchalin | |
| 4,738,527 A | * 4/1988 | McBrien | 356/5.05 |
| 5,220,403 A | 6/1993 | Batchelder et al. | |
| 5,956,355 A | * 9/1999 | Swanson et al. | 372/20 |
| 6,160,826 A | * 12/2000 | Swanson et al. | 372/20 |

* cited by examiner

Primary Examiner—Loha Ben
(74) Attorney, Agent, or Firm—Jeffrey Moy; Harry M. Weiss; Weiss, Moy & Harris P.C.

(57) ABSTRACT

A method and system for performing swept-wavelength measurements within an optical system provides improved operation in resonator-enhanced optical measurement and data storage and retrieval systems. The system includes an illumination subsystem having a swept-wavelength mode, a detection subsystem, an interferometer or an optical resonator interposed in an optical path between the illumination subsystem and the detection subsystem and a time domain analysis subsystem. Multiple resonance points of the optical resonator are detected by the time-domain subsystem when the illumination subsystem is in the swept-wavelength mode in order to determine resonator or interferometer characteristic changes. The resulting information can be used directly as a measurement output, or cavity length information may also be used to adjust the operating wavelength of a constant wavelength mode of the illumination subsystem.

22 Claims, 4 Drawing Sheets

METHOD AND SYSTEM FOR PERFORMING SWEPT-WAVELENGTH MEASUREMENTS WITHIN AN OPTICAL SYSTEM

RELATED APPLICATIONS

This application is a continuation-in part of U.S. patent application "SYSTEM OF BEAM NARROWING FOR RESOLUTION ENHANCEMENT AND METHOD THEREFOR", Ser. No. 09/789,913, filed on Feb. 21, 2001, now U.S. Pat. No. 6,522,471, and is further related to pending U.S. patent applications from which it claims the benefit of priority under 35 U.S.C. §120: OPTICAL STORAGE METHOD AND APPARATUS HAVING ENHANCED RESOLUTION", Ser. No. 09/871,512, filed May 30, 2001, now U.S. Pat. No. 6,700,840; "OPTICAL MEASUREMENT AND INSPECTION METHOD AND APPARATUS HAVING ENHANCED OPTICAL PATH DIFFERENCE DETECTION", Ser. No. 09/933,225, filed Aug. 20$^{th}$, 2001, now U.S. Pat. No. 6,653,649; "OPTICAL INSPECTION METHOD AND APPARATUS HAVING AN ENHANCED HEIGHT SENSITIVITY REGION AND ROUGHNESS FILTERING" Ser. No. 10/002,425, filed Oct. 23, 2001, now U.S. Pat. No. 6,714,295; and "METHOD AND SYSTEM FOR CONTROLLING RESONANCE WITHIN A RESONATOR-ENHANCED OPTICAL SYSTEM", Ser. No. 10/329,741, filed Dec. 23, 2002, now U.S. Pat. No. 6,717,707. The specifications all of the above-listed applications are incorporated herein by reference.

BACKGROUND OF THE INVENTION

1. Field of the Invention

This invention relates to optical systems, and more specifically, to optical systems that incorporating a coherent interference in either the illumination path or a measurement path.

2. Description of the Related Art

Optical measurement systems, optical storage and retrieval systems and other optical systems may be limited by many factors, including illumination beam size, diffraction limit, detector noise, and resolution. The above-incorporated patent applications disclose techniques for enhancing the performance of a variety of optical systems and improving the resolution and sensitivity of optical technologies disclosed therein.

It would be further desirable to improve the performance of the systems disclosed in the above-referenced patent applications, as well as other optical systems, in order to further improve their performance. The above-referenced patent application "METHOD AND SYSTEM FOR CONTROLLING RESONANCE WITHIN A RESONATOR-ENHANCED OPTICAL SYSTEM", discloses a method and system for resonance control by a closed-loop feedback system via control of effective optical cavity length either by adjusting the operating wavelength, the propagation constant of a path within the resonator or by adjusting the physical cavity length.

However, in certain applications it may not be practical to use such a feedback loop, especially when the control mechanism is the illumination wavelength, as the wavelength must be controlled very precisely for resonators having substantial path length (necessary for resonators having a high Q-factor). The system phase accuracy requirement in some measurement applications requires the wavelength control to meet or exceed 0.1% of the wavelength. Further, the resonator further multiplies deviations in phase by the cavity length. With a resonator length of 1000λ, phase control to 0.1% of the wavelength dictates control of the illumination wavelength to within 1 part per million, which is difficult or impossible to stably achieve while maintaining high speed operation by using a tunable illumination source and feedback loop.

Therefore, it would be desirable to provide an alternative method and system for measurement and resonator control that does not require a closed-loop continuous feedback system for adjusting cavity length or illumination wavelength.

SUMMARY OF THE INVENTION

The foregoing objectives are achieved in an optical system and method and apparatus for measurement and resonator control. The system includes a swept-wavelength optical illumination subsystem, an optical detection subsystem and a device for producing interference disposed in at least one optical path between the illumination system and the detection system. The device for producing interference may a standard interferometer, multi-beam interference device or an infinite beam interferometer such as an optical resonator.

The detection system further includes time-domain analysis stage that may be used to provide direct measurement output or measure resonant cavity length permitting open-loop adjustment of cavity length or interferometer phase. The output of the time-domain analysis stage may include information about the position of resonance or interference peaks, shape, width and height of peaks or other variations in the detected optical signal.

In particular, components of the time-domain analysis provide information about the changing resonant path length of the resonator, which may be a measurement function of the system, or may be used for adjusting the illumination wavelength or effective cavity length in an open-loop system.

The foregoing and other objects, features, and advantages of the invention will be apparent from the following, more particular, description of the preferred embodiment of the invention, as illustrated in the accompanying drawings.

DESCRIPTION OF EMBODIMENTS OF THE INVENTION

The above-incorporated patent applications describe various resonator-enhanced optical systems, such as optical storage data and retrieval systems having improved data density, illumination sources having narrowed beam widths and optical measurement systems having improved resolution and contrast and having improved detector phase/amplitude slope characteristics controlled over portions of the detector response. The above-recited improvements are developed by placement and tuning of resonators within the optical paths of the associated systems, in order to optimize the operating point on the resonator response function.

Figure 1:
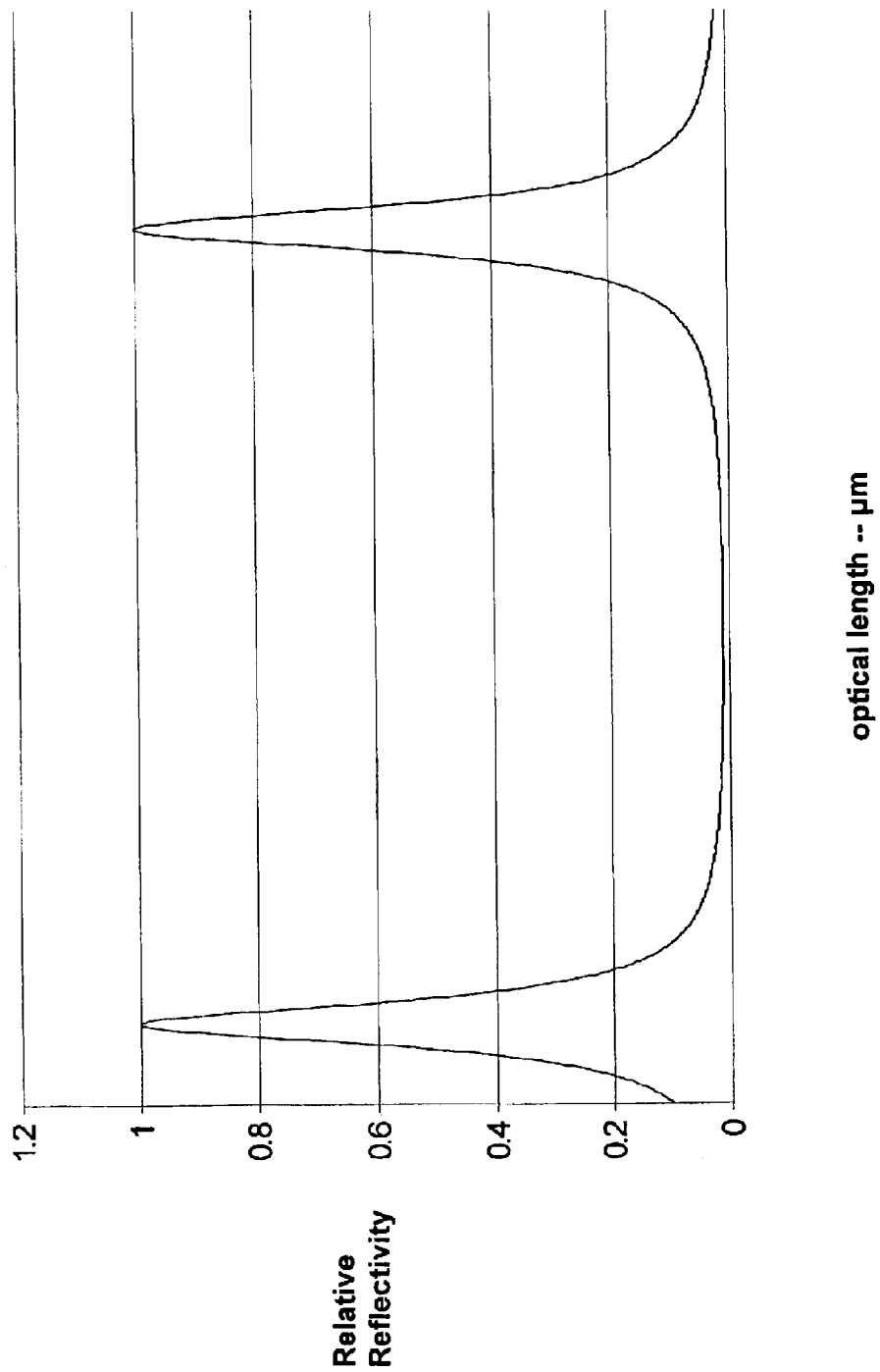
FIG. 1 is a graph depicting the response of an optical resonator in an optical system in accordance with an embodiment of the present invention.

While the incorporation of a resonator improves the performance of the systems described within the above-incorporated patent applications, the resonator generally must be tuned precisely to a specific point in the response function. The tuning requirement is made even more stringent when the resonator operating point is set slightly off of resonance, producing improved phase slope contrast for use in particular applications of embodiments of the present invention. With reference to FIG. 1, it is observed that the response curve of an optical resonator is very sharp near the resonances and almost flat for operating points between them, which corresponds to the physical basis for resonator sensitivity. Therefore, in the above-incorporated patent applications, the resonator is tuned so that the functioning point lies in the correct position on the response curve. The above-incorporated patent application: "METHOD AND SYSTEM FOR CONTROLLING RESONANCE WITHIN A RESONATOR-ENHANCED OPTICAL SYSTEM", provides a tuning mechanism for controlling resonator cavity length using a closed-loop feedback system.

Feedback control of the operating frequency and mechanical or electrical control of the cavity length have both been disclosed in the above-referenced patent application as a mechanism for maintaining the tuning of the various optical systems incorporating resonators described in the above-incorporated patent applications. However, as mentioned above, in some applications, it may be difficult or impossible to achieve a feedback control system that will properly maintain the tuning of the resonator, while maintaining the high speed operation required for most applications.

The present invention provides an alternative to tuned resonator measurement systems and an alternative tuning system that may be employed to tune the optical systems described in the above-incorporated patent applications. The measurement techniques use a time domain detection analysis that may be applied to both resonator and non-resonator optical systems such as interferometers. Rather than attempting to always maintain the effective resonator cavity length at a constant length or set the illumination wavelength to a wavelength that maintains the operating point of the resonator, the present invention uses time domain analysis to determine changes in the effective length of the cavity and/or to determine the absolute optical length of the cavity. The present invention also provides a measurement of other cavity changes, especially when a surface of the cavity is a surface under measurement with features detected by the time domain analysis, such as reflectivity/absorption, polarization, scattering (e.g. surface roughness), and so forth.

A swept wavelength illumination source is used to vary the effective cavity length through several discrete resonance points. The time domain relationship of the resonance points contains information about the cavity length, as the spread of the resonance points (detectable as pulses or other variations in the time domain detected signal) decreases with wavelength. Thus, both instantaneous changes in the detected signal time domain profile and the time domain profile it self can be analyzed to determine cavity length, cavity length changes or both. The time domain profile can be examined (or initially detected) to find any combination of pulse position, pulse width, pulse height and pulse shape. The information from the time domain analysis can be used to determine cavity length, resonance "Q" (which may indicate a gross variation in cavity length or a change in reflectivity/absorption/scattering, etc.)

The techniques of the present invention may also be extended to other optical systems such as interferometers, where while the intensity variation due to surface changes or other system parameters are not as great as for variations in resonator cavity length, the changes in local intensity maxima or minima positions or pulse shape as the wavelength is swept nevertheless can be detected and used to determine surface characteristics, optically encoded data and other changes within an optical system. All that is required is that a device for generating an interference be present in the optical path, that may be a multi-beam interference, an infinite beam interferometer forming an optical resonator such as a Fabry-Perot resonator, or a standard interferometer having a two-beam phase coherent combination.

Figure 2:
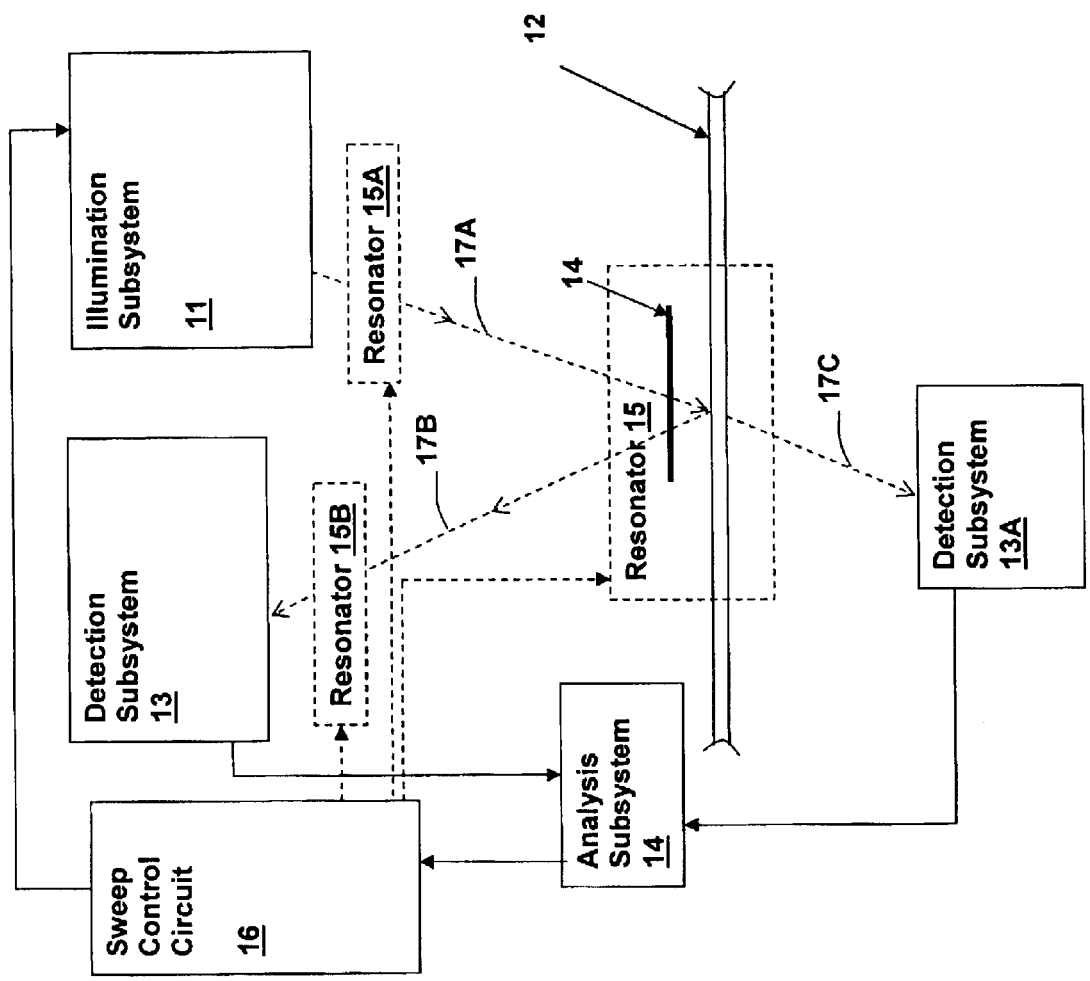
FIG. 2 is an illustration depicting an optical system in accordance with an embodiment of the present invention.

With reference now to FIG. 2, a surface or volume 12 including features under detection or data that is being extracted is illuminated by a tunable illumination subsystem 11 that produces illumination beam 17A. A reflected beam 17B and/or a transmitted beam 17C is detected by a detection subsystem 13 and/or 13A, providing measurement information or data extraction. A resonator 15, 15A or 15B is positioned within the optical path of the illumination beam 17A, reflected beam 17B and/or transmitted beam 17C. Illumination subsystem 11 has at least a swept-wavelength operating mode responsive to sweep control circuit 16, which sweeps illumination subsystem 11 through multiple resonant points of resonator 15, 15A or 15B. An analysis subsystem 14 determines a time-domain relationship between the resonances encountered by sweeping the illumination wavelength, and cavity length or changes in cavity length of resonator 15, 15A or 15B are thereby determined. The cavity length or changes therein may be used directly as a measurement output where the cavity length provides the desired measurement information. For example, in measurement systems where the features of surface or volume under measurement 12 cause variation in the cavity length of resonator 15, the information extracted by analysis subsystem 14 contains the feature information.

In an alternative open-loop feedback control system embodiment, the optical system may subsequently be tuned at a predetermined operating point in a constant-wavelength mode of illumination subsystem 11. With an operating wavelength determined in conformity with the determined cavity length or changes in cavity length of resonator 15, 15A or 15B to provide the desired characteristics at detection subsystem 13 and/or 13A.

In beam narrowing applications, resonator 15A is employed to reduce the profile of illumination beam 17A. Resonator 15A may be included within illumination subsystem 11 or located between illumination subsystem and surface 12 as shown. Alternatively, or in combination, resonator 15 may be employed at surface 12 to increase sensitivity of the optical system. Resonator 15 includes a partially reflective surface 14 positioned above surface 12 at a predetermined distance to provide a predetermined resonance operating point.

Detection subsystem 13 provides information to analysis subsystem 14 so that the time domain relationship of resonance points can be determined, which is generally a pulse-shaped variation in intensity level (which may be "dark" or "gray" level) of an interferometric fringe detection (e.g., a dark level detector. Analysis subsystem 14 extracts information relating to one or more of the pulse peak positions (and differences between pulse peak positions), pulse width, pulse height and pulse shape.

Tuning of resonator 15, 15A or 15B may or may not be implemented in systems in accordance with various embodiments of the present invention. Since the measurement system is capable of determining multiple resonance points and their time relationships when illumination subsystem 11 is in swept-wavelength mode, it may not be necessary or desirable to provide other than a generally fixed cavity length for resonator 15, 15A or 15B (ignoring the actual cavity length variations provided by surface under measurement 12). However, when it is desirable to tune resonator 15, 15A or 15B, tuning may be accomplished by various means, such as a mechanical positioner (provided by a piezoelectric element, voice coil or other positioning device), a dielectric having an electrically alterable dielectric constant or thickness within resonator 15, 15A or 15B, or other mechanisms as described in the above-incorporated patent applications.

Tuning (including sweeping) of illumination source 11 may be accomplished by use of a broadband laser/tunable filter such as the external cavity laser (ECL) or semiconductor tunable lasers such as Distributed-feedback (DFB) lasers, distributed Bragg reflector (DBR) lasers and vertical cavity surface emitting lasers (VCSEL).

Figure 3:
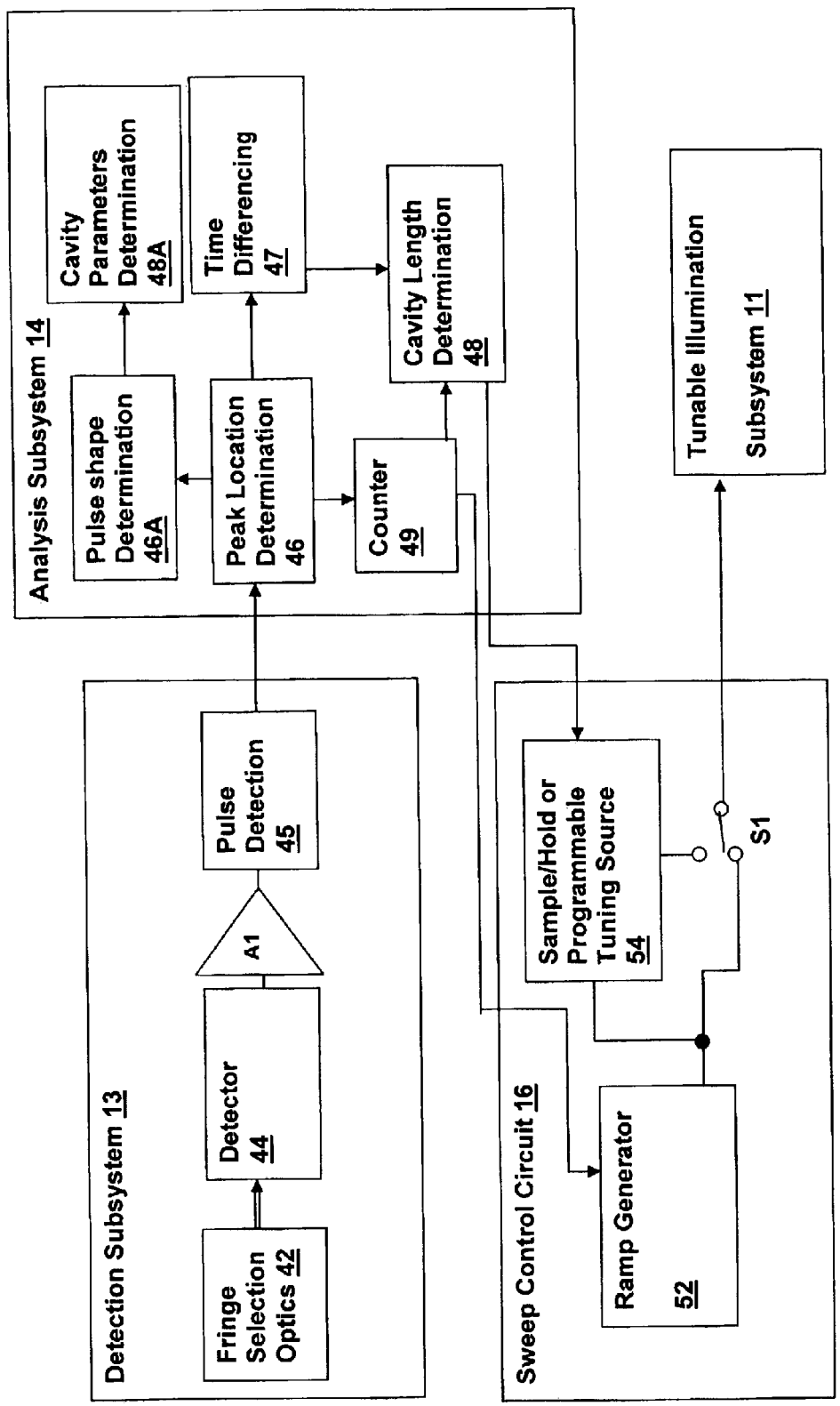
FIG. 3 is a block diagram showing details within the optical system of FIG. 2.

Referring now to FIG. 3, details of the detection and control systems in accordance with embodiments of the present invention are depicted. Detection subsystem 13 includes fringe selection optics 42 that select the interferometric detection point as the output to detector 44. Amplifier A1 adjusts the gain and offset of detector output 44 to provide a control signal to pulse detection circuit 45. Pulse detection circuit 45 is designed to match the shape of the pulses received by detection subsystem 13, which will generally follow the shape of the Airy-function (for a linearly changing illumination wavelength) that describes the characteristic response of the resonator with respect to wavelength (See FIG. 1). Pulse detection circuit 45 may be a matched filter or other correlation block, in order to maximize the received signal-to-noise ratio in conformity with a predictable pulse shape.

The output of detection subsystem 13 enters a peak location determination block 46 within analysis subsystem 14. Peak location determination block 46 determines a time relationship of multiple resonance peaks occurring in resonator 15, 15A or 15B as the wavelength of illumination subsystem 11 is swept in swept-wavelength mode. Peak location determination block may be a threshold comparator, but preferably a partial response detector or other precision pulse position estimation circuit having a characteristic suitably matched to the output of pulse detection circuit 45. Additionally, a maximum-likelihood detector may be included to further correlate the expected time locations of pulses as determined by the linearly-swept wavelength for a fixed cavity length, especially in applications where the time location set for a plurality of pulses is a non-contiguous functions, such as in optical detection systems using a reflector to form a resonator with the encoded surface, where detection subsystem 13 is attempting to discern and differentiate between two or more discrete cavity lengths.

A pulse shape determination block 46A is also coupled to an output of detection subsystem 13 and may measure the width, height or other shape characteristic of pulses received by detection subsystem 13. Width detection may be achieved using a threshold detection that measures the crossing points of a pulse through a particular threshold. Pulse symmetry may be detected by differentiating between the positive and negative transitions and comparing with the output of pulse shape determination block 46A. Pulse height may be measured by one or more thresholds, including analog-to-digital (A/D) conversion systems providing a quasi-continuous measurement range of pulse height.

Also, particular shapes may be correlated or a correlation to one or more predetermined shapes may be compared in order to determine the presence or absence of features on a surface under measurement or other measurement or optical data input to the system. A cavity parameters determination block 48A is coupled to the output of pulse shape determination block 46A for determining cavity parameters as a function of the pulse shape, such as reflectivity/absorption/scattering of a surface under measurement taken as a function of pulse width determined by pulse shape determination block.

Time differencing block 47 determines the differences between the multiple resonant peaks so that a cavity length determination block 48 can extract a cavity length or changes in cavity length of resonator 15, 15A or 15B. The cavity length information or change information may be used directly as a measurement output, for example when one of the resonator surfaces is a surface under measurement and variations in the height of the surface under measurement is the desired measurement or data detection output. A counter 49 is used to count the number of resonance points scanned through by the swept illumination wavelength and can be used to reset ramp generator 52 within sweep control circuit 16. Counter 49 thus ensures that a constant number of resonance points is scanned.

As an alternative to direct measurement output from analysis subsystem 14 while illumination subsystem 11 is in swept-wavelength mode, a sample/hold or programmable tuning source 54 may be used to provide a constant-wavelength mode for illumination source 11. A switch S1 provides selection of constant-wavelength mode vs. swept-wavelength mode and sample/hold may be used to sample a particular point in the ramp generator 52 sweep output corresponding to a particular resonance operating point (not necessarily a resonance peak) or the wavelength of illumination subsystem 11 may be programmed via a programmable register, divider, divider/multiplier loop or other means. Such a configuration provides open-loop control of the operating wavelength of tunable illumination source 11 while in constant-wavelength mode.

Figure 4:
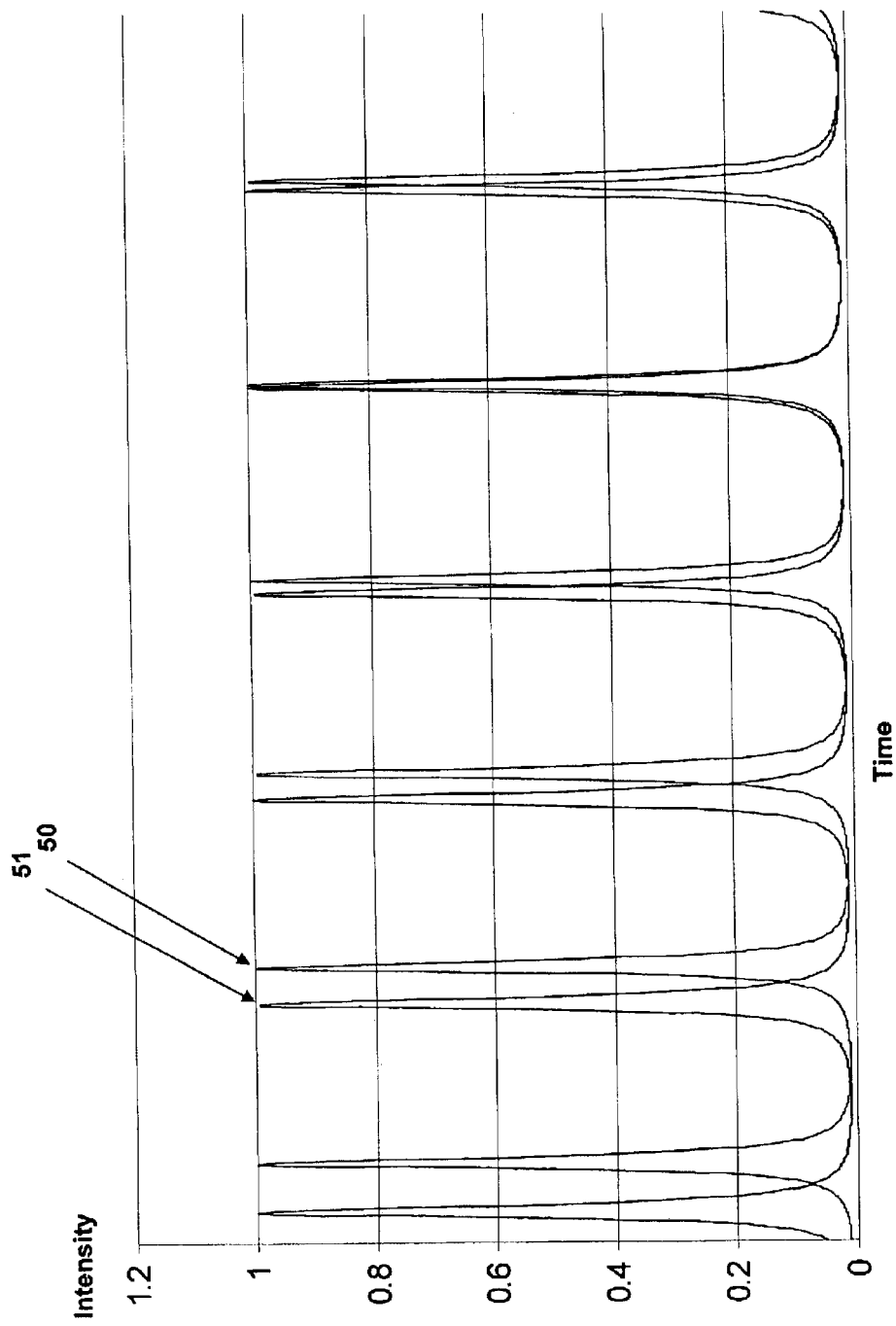
FIG. 4 is a graph depicting detected intensity in an optical system in accordance with an embodiment of the present invention.

Referring now to FIG. 4, detector 44 output signals (50, 51) as produced by embodiments of the present invention are depicted over time as the illumination wavelength is swept for two different cavity lengths over time in two identical frequency sweeps. Sweep 50 is for a cavity longer than the cavity length producing sweep 51, as the peaks are closer together. The longer the cavity, the more resonance points are present over a given range of swept wavelength.

The figure shows a detector 44 output when the detector is positioned on a light-band fringe position. It is apparent from the figure, that the position of the intensity peaks (which may be translated to intensity nulls for dark-band detector positions) in time, varies with the cavity length as described above. Peak location determination block 46 determines the exact position of the peaks (or nulls for a dark-band detector position) and the spread of the peaks in time is used to determine the cavity length according to the analysis below.

With the general notations, the optical path between the two plates is given by the known formula:

$$\delta = \frac{4\pi}{\lambda} nd\cos\theta' \qquad [1]$$

where $\lambda$ is the wavelength, d is the spacing between plates, n is the refractive index and $\theta$ is the incidence angle between the path and the plates. In a resonant cavity, the incidence angle θ is zero, and therefore the refracted one as well, so that:

$$\delta = \frac{2\pi}{\lambda} 2nd \quad [2]$$

giving a resonance for every:

$$2nd = m\lambda \quad [2a]$$

where m is a modal resonance number.

When the illumination wavelength is swept and by differentiating [2a] with respect to time the resulting equation applies:

$$d \cdot \frac{\partial n}{\partial t} dt + n \cdot \frac{\partial d}{\partial t} dt = \frac{\lambda}{2} \cdot \frac{\partial m}{\partial t} dt + \frac{m}{2} \cdot \frac{\partial \lambda}{\partial t} dt \quad [3]$$

Where, for a constant refractive index, $$\frac{\partial d}{\partial t} dt = \frac{\lambda}{2n} \cdot \frac{\partial m}{\partial t} dt + \frac{m}{2n} \cdot \frac{\partial \lambda}{\partial t} dt \quad [3a]$$

When "m" is large compared to "λ" and "∂"(which is the usual case), the first term in equation [3a] can be neglected, as it is small in comparison with the second, giving:

$$\frac{\partial d}{\partial t} dt = \frac{m}{2n} \cdot \frac{\partial \lambda}{\partial t} dt \quad [3b]$$

A change in the cavity length "d" is therefore equivalent—up to a factor—to a change in the wavelength, "λ".

Since the optical path difference between two cavity resonance points is equal to one wavelength (due to the round trip in the cavity), the result illustrated in [3b] proves that a change of the nominal wavelength with a factor of "1/m", will produce the same effect. When the wavelength is swept continuously over time, according to a given pattern, for example a saw tooth pattern, during the linear portion of the sweep, the wavelength varies constantly with time, and therefore the resonance points will be detected as if the cavity length has changed correspondingly.

Since the variation of the wavelength is constant with time, one can consider—up to the first approximation—that the time difference between two neighboring resonance points is also constant and given by the formula [3b]. If there is a change in the cavity length while the wavelength sweeps, the distance between the resonances changes according to formula [2a], providing a time domain measurement of the change in the cavity. The change can be a change in position, shape, or height of the pulses produced by sweeping through the resonance (or interference slope for an interferometer) generated by any change in the optical path, such as a movement of the mirrors, a defect or change in the mirrors' optical characteristics, a change in the refractive index of the cavity, and so forth. Therefore detection of the spread and shape of the resonance peaks by the detection subsystem can be directly translated to determine cavity characteristics, either dynamically when the cavity is a parameter under measurement (as in the surface inspection systems or data storage systems described in the above-incorporated patent applications) or quasi-statically as in beam-narrowing applications.

While the invention has been particularly shown and described with reference to the preferred embodiments thereof, it will be understood by those skilled in the art that the foregoing and other changes in form, and details may be made therein without departing from the spirit and scope of the invention.

What is claimed is:

1. An optical system comprising:
   an optical illumination subsystem for producing an optical beam, said optical illumination subsystem including a swept-wavelength operating mode;
   a device for generating a coherent interference within a path of said beam;
   an optical detection subsystem for measuring an intensity of light leaving said interference; and
   a time domain analysis subsystem coupled to said optical detection subsystem for extracting a time relation of particular points of intensity variations produced by said interference when said optical illumination subsystem is operated in said swept-frequency operating mode.

2. The optical system of claim 1, wherein said device for generating a coherent interference includes a surface under measurement for producing one or more reflections forming part of said interference, and wherein said time domain analysis subsystem determines characteristics of said surface from said time relation of said particular intensity points.

3. The optical system of claim 1, wherein said particular intensity points are local intensity maxima.

4. The optical system of claim 1, wherein said particular intensity points are local intensity minima.

5. The optical system of claim 1, wherein said device for generating a coherent interference comprises an optical resonator positioned in an optical path between said optical illumination subsystem and said optical detection subsystem, whereby performance of said optical system is enhanced at particular resonant operating points within said optical resonator, and wherein said time domain analysis subsystem extracts a time relation of particular resonant operating points of said optical resonator when said optical illumination subsystem is operated in said swept-frequency operating mode.

6. The optical system of claim 5, wherein said time domain analysis subsystem determines one or more optical characteristics of said optical resonator in conformity with a time relation of two or more of said particular resonant operating points.

7. The optical system of claim 6, wherein said one or more optical characteristics is an optical length of said resonator.

8. The optical system of claim 7, wherein said time domain analysis subsystem further compares said determined optical length to a predetermined desired optical length and further comprising a tuning mechanism for adjusting said optical length of said optical resonator in conformity with differences between said determined optical length and said predetermined desired optical length.

9. The optical system of claim 5, wherein said time domain analysis subsystem determines a change in optical characteristics of said optical resonator in conformity with a change in time relation of two or more of said particular resonant operating points.

10. The optical system of claim 5, wherein said time domain analysis subsystem determines a measurement output of said optical system in conformity with a change in said time relation of two or more of said particular resonant operating points.

11. The optical system of claim 1, wherein said time domain analysis subsystem determines a measurement output of said optical system in conformity with a change in said time relation of two or more of said particular intensity points.

12. The optical system of claim 1, wherein the time domain analysis subsystem comprises a matched filter having a characteristic shape matched for reception to the shape of the variation of an output of said optical detection subsystem as an operating wavelength of said illumination subsystem is swept.

13. The optical system of claim 1, wherein said time domain analysis subsystem comprises a partial response detector for determining peak position of pulses received by said time domain analysis subsystem as an operating wavelength of said illumination subsystem is swept.

14. The optical system of claim 1, wherein said time domain analysis subsystem comprises a detector for determining a shape of pulses received by said detection subsystem as an operating wavelength of said illumination subsystem is swept.

15. The optical system of claim 1, wherein said time domain analysis subsystem comprises a detector for determining an amplitude of pulses received by said detection subsystem as an operating wavelength of said illumination subsystem is swept.

16. The optical system of claim 1, wherein said time domain analysis subsystem comprises a maximum likelihood detector for determining a most likely data pattern in conformity with a position of pulses received by said time domain analysis subsystem as an operating wavelength of said illumination subsystem is swept.

17. The optical system of claim 1, wherein said device for generating a coherent interference comprises an interferometer and wherein said particular intensity points are variations in intensity of a predetermined fringe of said interferometer produced by sweeping of an illumination wavelength of said optical illumination subsystem.

18. An optical system comprising:

an optical illumination subsystem for producing an illumination beam, said optical illumination subsystem including a swept-wavelength operating mode;

a device for generating an interference within a path of said beam;

an optical detection subsystem for measuring an intensity of light that has left said interference; and means for extracting a time relation of particular intensity detected by said optical detection subsystem when said optical illumination subsystem is operated in said swept-frequency operating mode.

19. The optical system of claim 18, further comprising means for enhancing the performance of said optical system at particular resonant operating points, and wherein said extracting means extracts a time relation of particular resonant operating points of said enhancing means.

20. A method for operating an optical system, said method comprising:

generating an illumination beam from an illumination subsystem, said illumination beam having a swept-wavelength;

introducing a coherent interference in a path of said illumination beam;

detecting light leaving said interference with a detection subsystem; and determining a time relationship of particular intensity points of said detected light, whereby variations within a surface under test of said optical system are detected.

21. The method of claim 20, wherein said coherent interference is generated by one or more reflections from said surface under test, and wherein said determining detects variations within said surface.

22. The method of claim 20, further comprising enhancing performance of said illuminating and said detecting by providing said interference from a resonator positioned between said illumination subsystem and said detection subsystem, and wherein said determining determines a time relation of multiple resonance points of said resonator as said illumination beam wavelength is swept.

* * * * *